(12) United States Patent
Mitchell

(10) Patent No.: US 10,918,145 B1
(45) Date of Patent: Feb. 16, 2021

(54) DOUBLE GLOVES

(71) Applicant: DG Tab, LLC, Richmond Heights, OH (US)

(72) Inventor: Marian Mitchell, Richmond Heights, OH (US)

(73) Assignee: DG TAB, LLC, Richmond Heights, OH (US)

( * ) Notice: Subject to any disclaimer, the term of this patent is extended or adjusted under 35 U.S.C. 154(b) by 0 days.

(21) Appl. No.: 15/928,284

(22) Filed: Mar. 22, 2018

Related U.S. Application Data

(60) Provisional application No. 62/474,779, filed on Mar. 22, 2017.

(51) Int. Cl.
  *A41D 19/00* (2006.01)
  *A61B 42/10* (2016.01)

(52) U.S. Cl.
  CPC ....... *A41D 19/001* (2013.01); *A41D 19/0058* (2013.01); *A41D 19/0093* (2013.01); *A61B 42/10* (2016.02)

(58) Field of Classification Search
  CPC .............. A41D 19/001; A41D 19/0058; A41D 19/0093; A61B 42/10
  See application file for complete search history.

(56) References Cited

U.S. PATENT DOCUMENTS

| | | | |
|---|---|---|---|
| 4,876,747 A | 10/1989 | Coffey et al. | |
| 5,349,705 A * | 9/1994 | Ragan | A41D 19/0006 2/161.6 |
| 5,467,483 A | 11/1995 | Saadatmanesh et al. | |
| 5,679,399 A * | 10/1997 | Shlenker | A61B 42/10 427/2.3 |
| 5,966,741 A * | 10/1999 | Klecina | A41D 19/0068 2/159 |
| 7,665,150 B2 * | 2/2010 | Holley | A41D 19/0044 2/16 |
| 9,072,325 B2 * | 7/2015 | Ragan | A41D 19/015 |
| 2005/0060787 A1 * | 3/2005 | Cheng | A41D 19/0058 2/161.7 |
| 2007/0061942 A1 | 3/2007 | Schrödl | |
| 2007/0124849 A1 * | 6/2007 | Williams | A41D 19/0006 2/275 |

(Continued)

OTHER PUBLICATIONS

New surgical glove alleviates need for "double gloving"; Mar. 22, 2004; URL: https://www.news-medical.net/news/2004/03/22/69.aspx.

(Continued)

*Primary Examiner* — Khaled Annis

(57) ABSTRACT

A glove assembly including two or more elastomeric gloves removably attached to one another, said two or more gloves attached to one another by a graspable attachment member, and a method of simultaneously inserting a hand into two or more elastomeric gloves. Previously known double gloving required users to put each glove on one at a time, which could require a significant amount of time and may risk exposing the first glove to contaminants. Removably attaching the inner and outer gloves of the present disclosure may allow a user to easily don both gloves simultaneously, which allows the user to don both gloves in less time than previously known methods of double gloving.

11 Claims, 3 Drawing Sheets

(56) References Cited

U.S. PATENT DOCUMENTS

| | | |
|---|---|---|
| 2013/0067638 A1* | 3/2013 | Patkov ............. A41D 19/01505 2/168 |
| 2014/0289931 A1* | 10/2014 | Patkov ............. A41D 19/01505 2/168 |
| 2018/0027902 A1 | 2/2018 | Thompson et al. |
| 2018/0194539 A1* | 7/2018 | Ma ........................ A61B 42/40 |
| 2018/0271330 A1* | 9/2018 | Rampersd ............... A47J 43/28 |
| 2019/0142192 A1* | 5/2019 | Rampersd ............. A61F 13/105 294/99.2 |

OTHER PUBLICATIONS

BioBarrier, Inc.; 510(k) K060030 Summary; Jun. 27, 2006; Food and Drug Administration.

* cited by examiner

DOUBLE GLOVES

This application claims priority of Provisional Application No. 62/474,779 filed Mar. 22, 2017, which is hereby incorporated herein by reference.

FIELD OF INVENTION

The present invention relates generally to gloves, and more particularly to double gloves that are elastomeric.

BACKGROUND

Elastomeric gloves are often used for various tasks where a user does not wish to spread contamination to or from their hands. For example, surgeons wear elastomeric gloves during to prevent contaminants from the surgeons' hands from entering a patient being operated on. Also, hair stylists wear elastomeric gloves at times to prevent contaminants, such as hair dye, from staining the stylists skin.

Elastomeric gloves are utilized for many other applications, such as dentistry, laboratory testing, etc. At times users wear two gloves on each hand (i.e., wearing an inner glove and an outer glove on each hand) known as "double gloving." Double gloving offers some added protection to the user since the elastomeric materials of the two gloves combined are thicker than one of the gloves individually.

Double gloving also allows the user to perform a task (e.g., part of a surgery) where the outer pair of gloves contact an object or contaminant, remove the contaminated outer gloves, and then perform another task (e.g., another part of the surgery) where the inner pair of gloves contact another object or contaminant. Previously known methods of double gloving required users to put each glove on one at a time.

SUMMARY OF INVENTION

The present invention provides a glove assembly including two or more elastomeric gloves removably attached to one another, two or more gloves attached to one another by a graspable attachment member, and/or a method of simultaneously inserting a hand into two or more elastomeric gloves. Previously known double gloving required users to put each glove on one at a time, which could require a significant amount of time and may risk exposing the first glove to contaminants. Removably attaching the inner and outer gloves of the present disclosure may allow a user to easily don both gloves simultaneously, which allows the user to don both gloves in less time than previously known methods of double gloving.

The inner and/or outer gloves of the present disclosure may be sterilized. Contamination of the inner glove prior to removal of the outer glove may be reduced compared to previously known methods of double gloving since the inner glove could be disposed within the outer glove until the user removes the outer glove.

Once the outer glove is contaminated or otherwise desired to be removed, the user may easily detach the outer glove from an inner glove so that the inner glove remains on the user's hand. For example, a graspable attachment member may removably attach the inner and outer gloves. The user may grasp the graspable attachment member to detach the gloves to allow the outer glove to be quickly removed from the inner glove. A portion of the graspable attachment member may be at least partially formed by a tab that remains attached to the outer glove, which allows the user to remove the outer glove while avoiding transferring contaminants from the outer glove to the inner glove.

In an embodiment, the inner and outer gloves are simultaneously removed. For example, the user may grasp the graspable attachment member and simultaneously remove the inner and outer gloves from the user's hand. The inner and outer gloves would not need to be detached prior to removal.

The removable attachment, the graspable attachment member, and the method of simultaneously inserting the hand may be independently combined with one another or utilized separately. Thus, a glove assembly or method according to the present disclosure may include all of, any one of, or any combination of the removable attachment, the graspable attachment member, and the method of simultaneously inserting the hand.

According to one aspect of the disclosure, a glove assembly that includes an inner elastomeric glove with an inner cuff and a plurality of inner fingers, an outer elastomeric glove with an outer cuff and a plurality of outer fingers, the inner cuff and the plurality of inner fingers being concentrically disposed within the respective outer cuff and the plurality of outer fingers, and the inner cuff and the outer cuff being removably attached to one another.

According to another aspect of the disclosure, a glove assembly that includes an inner glove with an inner cuff and a plurality of inner fingers, an outer glove with an outer cuff and a plurality of outer fingers, the inner cuff and the plurality of inner fingers being concentrically disposed within the respective outer cuff and the plurality of outer fingers, and a graspable attachment member that attaches the inner cuff to the outer cuff.

According to another aspect of the disclosure, a method that includes inserting a user's hand simultaneously into an inner elastomeric glove and an outer elastomeric glove, the inner elastomeric glove being disposed within the outer elastomeric glove.

The foregoing and other features of the invention are hereinafter described in greater detail with reference to the accompanying drawings.

DETAILED DESCRIPTION

The principles of this present application have particular application to elastomeric double glove assemblies for preventing particulates and other contaminants from transferring to or from the user, such as from a surgeon's hands to a patient or vice versa, and thus will be described below chiefly in this context. It will be appreciated that principles of this invention may be applicable to other double glove assemblies.

Figure 1:
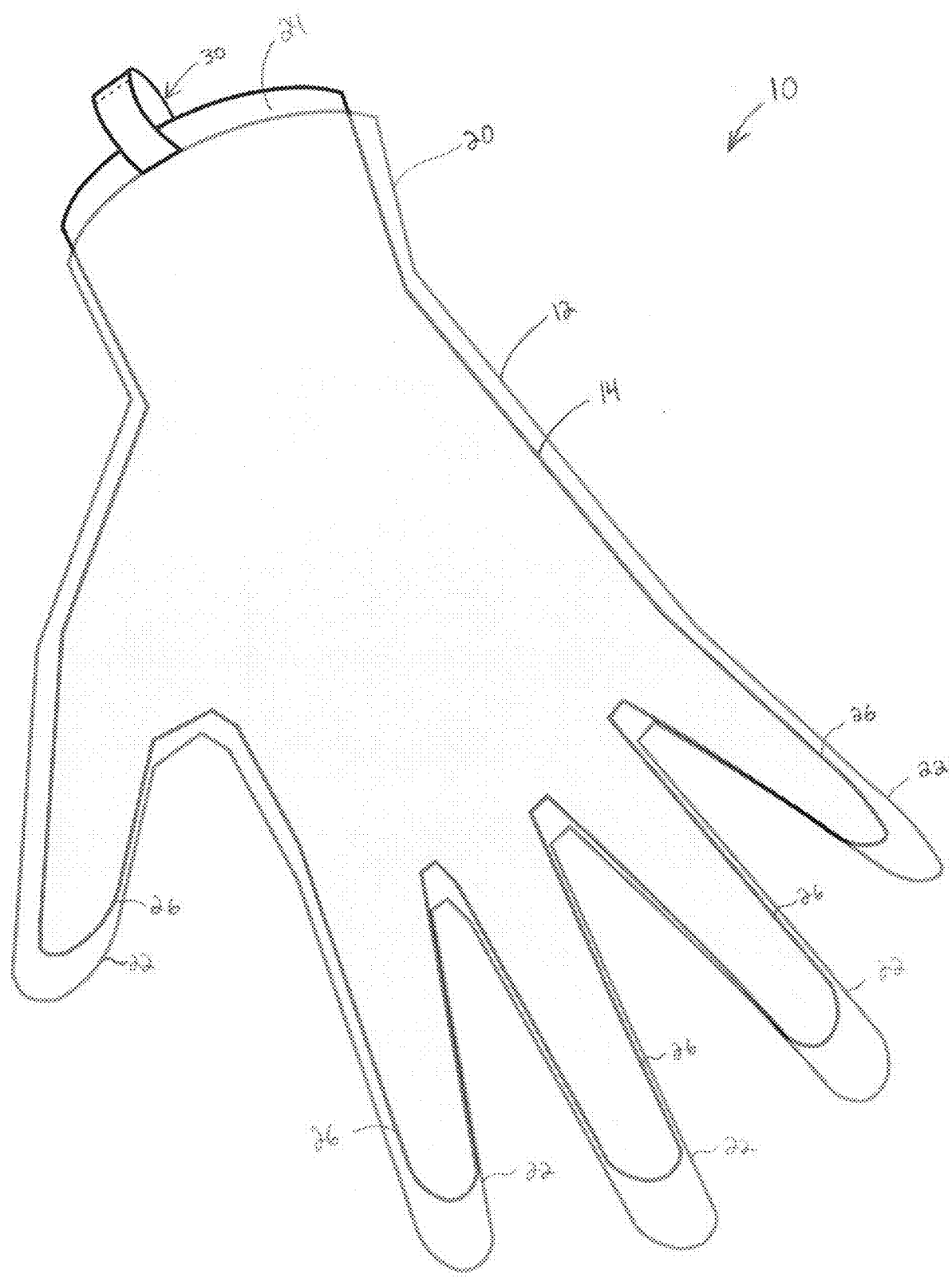
FIG. 1 is an oblique top view of an exemplary glove assembly including an exemplary graspable attachment member that removably attaches an inner and outer glove of the glove assembly.

Referring now in detail to the drawings, and initially to FIG. 1, a glove assembly 10 is illustrated. The glove assembly 10 may include an outer elastomeric glove 12 and an inner elastomeric glove 14 disposed within the outer elastomeric glove 12. The outer elastomeric glove 12 is illustrated as semi-translucent so that the inner elastomeric glove 14 can be seen. In an embodiment, the inner glove and the outer glove may be different colors. For example, the inner glove may be green and the outer glove may be white or translucent. In an embodiment, each elastomeric glove is made of vinyl and/or latex.

The outer elastomeric glove 12 may include an outer cuff 20 and outer fingers 22 that extend away from the outer cuff 20. The outer elastomeric glove 12 may be configured to receive the user's hand such that each of the user's fingers of the corresponding hand fits within the corresponding outer finger 22, and such that the user's corresponding wrist fits within the outer cuff 20.

The inner elastomeric glove 14 may include an inner cuff 24 and inner fingers 26 that extend away from the inner cuff 24. The inner elastomeric glove 14 may be configured to receive the user's hand such that each of the user's fingers of the hand fits within the corresponding inner finger 26, and such that the user's wrist fits within the inner cuff 24. The inner cuff 24 and the inner fingers 26 may be concentrically disposed within the respective outer cuff 20 and the outer fingers 22.

In an embodiment, the inner elastomeric glove is identical to the outer elastomeric glove. For example, the shape and size of each elastomeric glove may be identical when both are in an unstretched state. In another embodiment, the outer elastomeric glove is slightly larger than the inner elastomeric glove to accommodate the inner elastomeric glove between the outer elastomeric glove and the user's hand.

Referring still to FIG. 1 and later to FIG. 2, the glove assembly 10 may include a graspable attachment member 30 that removably attaches the inner cuff 24 to the outer cuff 20.

Figure 2:
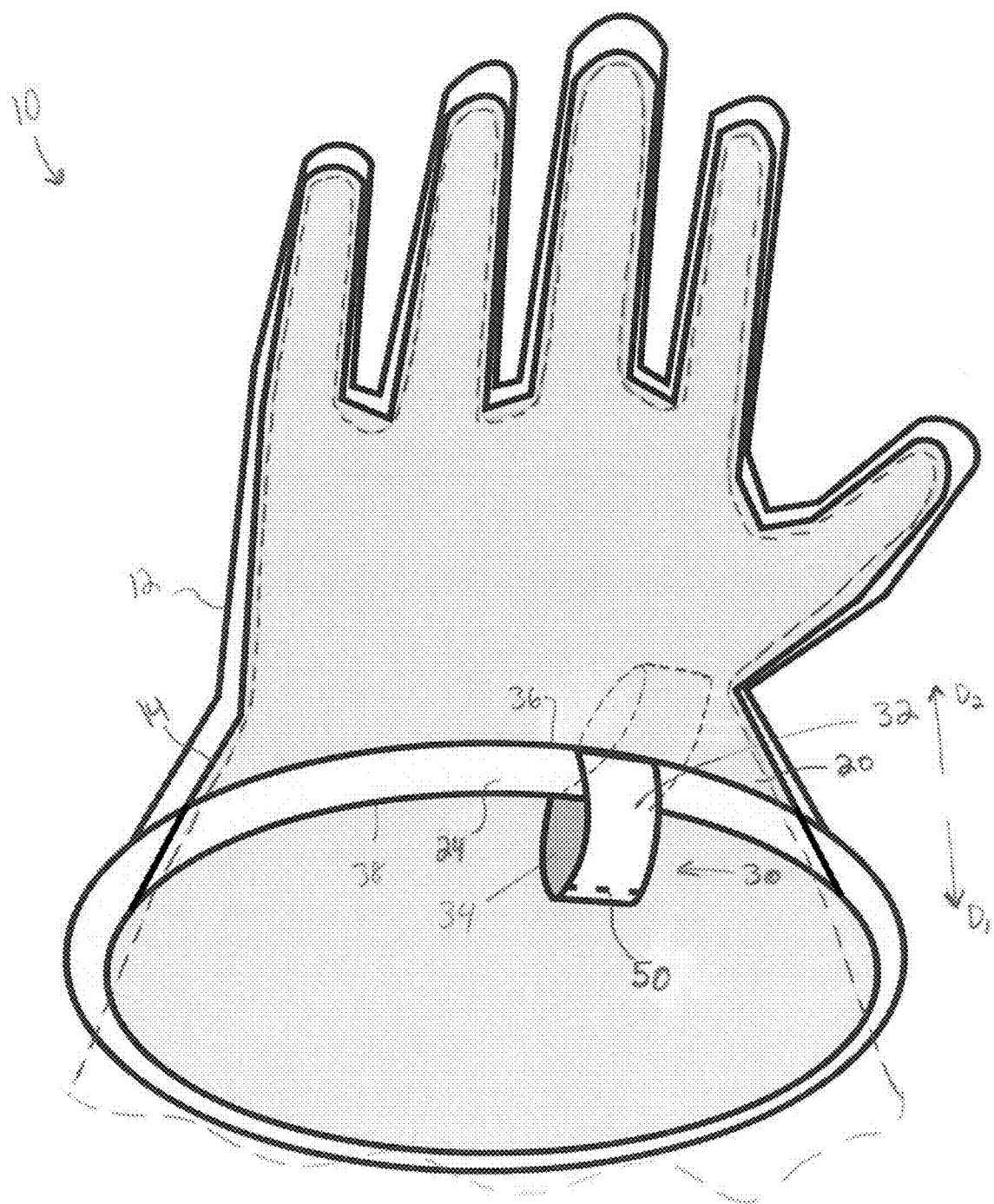
FIG. 2 is an oblique rear view of the glove assembly of FIG. 1.

Turning to FIG. 2, the graspable attachment member 30 may include a first portion, that may be at least partially formed by an outer tab 32, attached to the outer cuff 20 and may include a second portion, that may be at least partially formed by an inner tab 34, attached to the inner cuff 24. The outer tab 32 may be attached to a lip 36 of the outer cuff 20. The inner tab 34 may be attached to a lip 38 of the inner cuff 24.

The tabs 32 and 34 may each be relatively rigid compared to the elastomeric gloves 12 and 14. For example, the outer tab 32 and/or the inner tab 34 may be made of a material (e.g., vinyl or latex) that is thicker than an average thickness of the material forming either of the elastomeric gloves 12 or 14.

The graspable attachment member 30 may include a relatively weak portion (e.g., a perforated portion 50) that is configured to allow the outer tab 32 to detach from the inner cuff 24. The perforated portion 50 may be between the outer tab 32 and the inner tab 34, which allows the inner tab 34 to remain attached to the inner cuff 24 if the outer tab 32 is detached. In an embodiment, the graspable attachment member includes a peelable adhesive or a relatively thin portion that removably attaches the first portion to the inner cuff.

The outer tab 32 may extend radially outward from the lip 36 so that the user may easily grasp the outer tab 32 with the user's free hand or so that the user can put one of the fingers of the free hand in a partial loop formed by the tabs 32 and 34 while in an attached state. For example, as shown in dashed lines, the outer tab 32 and/or the inner tab 34 may flex or rotate relative to the corresponding lip 36 or 38 so that the outer tab 32 and/or the inner tab 34 extend radially outward from the corresponding lip 36 or 38.

Still referring to FIG. 2, the user may don the glove assembly 10 by inserting one of the user's hands (shown in dashed lines) simultaneously into the outer elastomeric glove 12 and the inner elastomeric glove 14. The user may insert the user's hand, fingers first, into the outer cuff 20 and the inner cuff 24 simultaneously. Simultaneously inserting the hand into both gloves 12 and 14 in one step allows the user to double glove their hand in less time than previous multi-step methods. In an embodiment, the user simultaneously inserts the user's hands into more than two gloves. For example, three or more gloves.

The user may grasp the outer tab 32 and/or the inner tab 34 and tension the corresponding outer cuff 20 and/or inner cuff 24 while the user's hand is being inserted. During insertion, the outer cuff 20 and the inner cuff 24 both move relative to the user's hand. The user's free hand may pull the outer tab 32 and/or the inner tab 34 in a direction $D_1$ (e.g., up a forearm (not shown) of the user that corresponds to the hand being inserted). In an embodiment, during insertion, the user's hand being inserted moves relative to the outer cuff and to the inner cuff, and the tabs are stationary or move less than the user's hand.

The user may simultaneously remove the inner elastomeric glove 14 and the outer elastomeric glove 12 at least partially by tensioning of the outer cuff 20 and the inner cuff 24. For example, the user may grasp the outer tab 32 and/or the inner tab 34 such that the inner cuff and the outer cuff are tensioned. During removal, the outer cuff 20 and the inner cuff 24 both move relative to the user's hand. The user's free hand may pull the outer tab 32 and/or the inner tab 34 in a direction $D_2$ (e.g., down the user's forearm that corresponds to the hand being removed) that is opposite the direction $D_1$. In an embodiment, during removal, the user's hand being removed moves relative to the outer cuff and to the inner cuff, and the tabs are stationary or move less than the user's hand.

Figure 3:
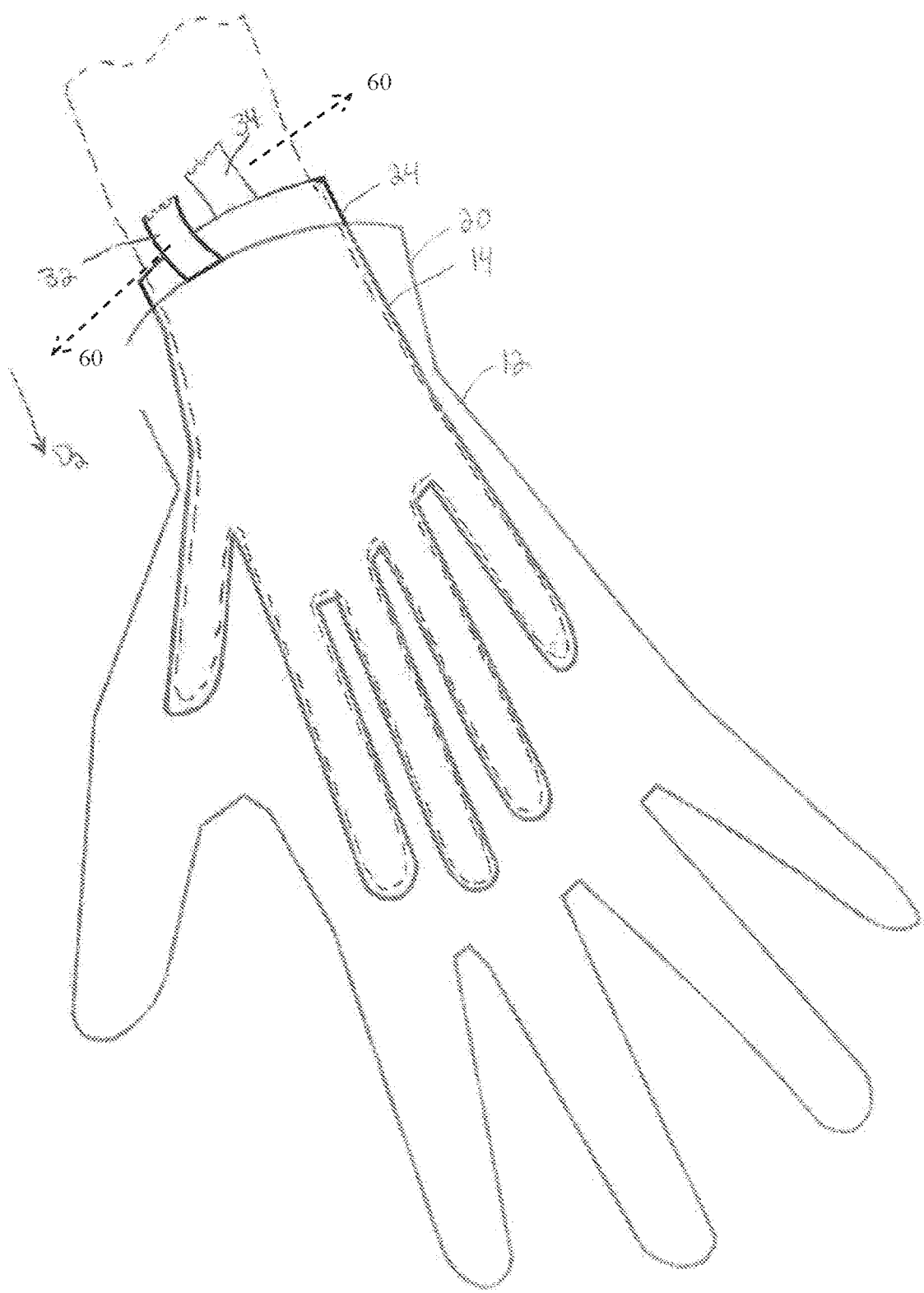
FIG. 3 is an oblique top view of the glove assembly in a detached state.

Turning now to FIG. 3 with brief reference to FIG. 2, the user may detach the outer cuff 20 and inner cuff 24. Detaching the outer cuff 20 and inner cuff 24 allows the user to remove the outer elastomeric glove 12 without removing the inner elastomeric glove 14 from on the user's hand (shown in dashed lines). A predetermined tension force 60 applied to respective opposite ends of the outer tab 32 and the inner tab 34 may detach the tabs 32 and 34 from one another.

Referring briefly to FIG. 2, as mentioned above with regards to the tabs 32 and 34 in the attached state, the user may grasp the outer tab 32 or insert a finger in the partial loop formed by the tabs 32 and 34. While the outer tab 32 is grasped or the finger is inserted, the user may tension the perforated portion 50 with enough force to tear the perforated portion 50 until the tabs 32 and 34 are in a detached state shown in FIG. 3. For example, the user may grasp the outer tab 32 and pull the outer tab 32 away from the inner tab 34 until the perforated portion 50 is torn such that the tabs 32 and 34 are completely detached.

Referring again to FIG. 3, in the detached state the outer tab 32 is detached from the inner cuff 24 such that tensioning the outer tab 32 can tension the outer cuff 30 without tensioning the inner cuff 24. The user may remove the outer elastomeric glove 12 at least partially by tensioning of the outer cuff 20. For example, the user may grasp the outer tab 32 such that the outer cuff 20 is tensioned.

During removal of the outer elastomeric glove 12 while in the detached state, the outer cuff 20 moves relative to the user's hand and to the inner cuff 24. For example, the user's free hand may pull the outer tab 32 in the direction $D_2$ down the user's forearm that corresponds to the hand being removed. In an embodiment, during removal, the user's hand being removed moves relative to the outer cuff, and the outer tab is stationary or moves less than the user's hand.

After the outer elastomeric glove 12 is removed, as mentioned above, the inner elastomeric glove 14 may be sterile (e.g., free from contaminants that contacted the outer elastomeric glove 12, such as bodily fluids or hair dye). The inner elastomeric glove 14 being free from contaminants allows the user to continuing wearing and using the inner elastomeric glove 14.

The user may remove the inner elastomeric glove 14 at least partially by the tensioning of the inner cuff 24. For example, the user may grasp the inner tab 34 such that the inner cuff 24 is tensioned. During removal of the inner elastomeric glove 14 while in the detached state, the inner cuff 24 moves relative to the user's hand. For example, the user's free hand may pull the inner tab 34 in the direction $D_2$ down the user's forearm that corresponds to the hand being removed. In an embodiment, during removal, the user's hand being removed moves relative to the inner cuff, and the inner tab is stationary or moves less than the user's hand.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A glove assembly including:
    an inner elastomeric glove with an inner cuff and a plurality of inner fingers;
    an outer elastomeric glove with an outer cuff and a plurality of outer fingers, wherein said inner cuff and said plurality of inner fingers are concentrically disposed within the respective said outer cuff and said plurality of outer fingers; and
    a single, graspable attachment member, said single, graspable attachment member comprising a first outer tab portion attached to said outer cuff, a second inner tab portion attached to said inner cuff, and a perforated portion disposed therebetween, said first outer tab portion being attached to said second inner tab portion only at said perforated portion.

2. The glove assembly of claim 1, wherein said perforated portion detaches said first portion from said inner cuff.

3. The glove assembly of claim 2, wherein a predetermined tension force applied to respective opposite ends of said first outer tab portion and said second inner tab portion may tear said perforated portion and detach said inner cuff from said outer cuff.

4. The glove assembly of claim 1, wherein each elastomeric glove is made of at least one of vinyl and latex.

5. The glove assembly of claim 1, wherein said inner elastomeric glove is identical to said outer elastomeric glove.

6. The glove assembly of claim 1, wherein said single, graspable attachment member is comprised of material that is thicker than the average thickness of the material from either of said inner glove or said outer glove.

7. A glove assembly including:
    an inner glove with an inner cuff and a plurality of inner fingers;
    an outer glove with an outer cuff and a plurality of outer fingers, wherein said inner cuff and said plurality of inner fingers are concentrically disposed within the respective said outer cuff and said plurality of outer fingers; and
    a single, graspable attachment member comprising a first outer tab portion attached to said outer cuff, a second inner tab portion attached to said inner cuff, and a perforated portion disposed therebetween, said first outer tab portion being attached to said second inner tab portion only at said perforated portion;
    said first outer tab portion being physically separated from said second inner tab portion, other than at said perforated portion.

8. The glove assembly of claim 7, wherein said graspable attachment member extends radially outward from said outer cuff.

9. The glove assembly of claim 8, wherein said graspable attachment member further includes a radially outwardly extending tab that at least partially forms said first outer tab portion, wherein said radially outwardly extending tab is attached to said outer cuff, and is removably attached to said inner cuff.

10. The glove assembly of claim 7, wherein said perforated portion detaches said first outer tab portion and said second inner tab portion upon application of a predetermined tension force applied to respective outer ends of said outer tab and said inner tab.

11. The glove assembly of claim 7, wherein said single, graspable attachment member is comprised of material that is thicker than the average thickness of the material from either of said inner glove or said outer glove.

* * * * *